US009095385B2

(12) United States Patent
Wallenstein et al.

(10) Patent No.: US 9,095,385 B2
(45) Date of Patent: Aug. 4, 2015

(54) ADJUSTABLE SPINAL IMPLANT INSERTION INSTRUMENT (71) Applicant: K2M, Inc., Leesburg, VA (US)

(72) Inventors: Todd Wallenstein, Ashburn, VA (US); George Miz, Palos Park, IL (US); John I Williams, Fort Wayne, IN (US)

(73) Assignee: K2M, Inc., Leesburg, VA (US)

( * ) Notice: Subject to any disclaimer, the term of this patent is extended or adjusted under 35 U.S.C. 154(b) by 149 days.

(21) Appl. No.: 13/683,202

(22) Filed: Nov. 21, 2012

(65) Prior Publication Data
US 2014/0142642 A1    May 22, 2014

(51) Int. Cl.
*A61B 17/70* (2006.01)
*A61F 2/44* (2006.01)
*A61F 2/46* (2006.01)
*A61F 2/30* (2006.01)

(52) U.S. Cl.
CPC ........... *A61B 17/7074* (2013.01); *A61F 2/4465* (2013.01); *A61F 2/4611* (2013.01); *A61F 2002/30795* (2013.01); *A61F 2002/30797* (2013.01); *A61F 2002/30904* (2013.01); *A61F 2002/4475* (2013.01); *A61F 2002/4624* (2013.01); *A61F 2002/4627* (2013.01); *A61F 2002/4628* (2013.01); *A61F 2002/4629* (2013.01)

(58) Field of Classification Search
USPC ............... 606/86 A, 86 R, 99, 100, 246, 279; 623/17.11–17.16
See application file for complete search history.

(56) References Cited

U.S. PATENT DOCUMENTS

| 5,425,772 | A | 6/1995 | Brantigan |
| 5,443,514 | A | 8/1995 | Steffee |
| 5,860,973 | A | 1/1999 | Michelson |
| 5,910,141 | A | 6/1999 | Morrison et al. |
| 5,968,098 | A | 10/1999 | Winslow |
| 6,143,032 | A | 11/2000 | Schafer et al. |
| 6,174,311 | B1 | 1/2001 | Branch et al. |
| 6,238,435 | B1 | 5/2001 | Meulink et al. |
| 6,325,827 | B1 | 12/2001 | Lin |
| 6,447,547 | B1 | 9/2002 | Michelson |
| 6,482,233 | B1 | 11/2002 | Aebi et al. |
| 6,579,318 | B2 | 6/2003 | Varga et al. |
| 6,676,703 | B2 | 1/2004 | Biscup |
| 6,712,819 | B2 | 3/2004 | Zucherman et al. |
| 6,719,794 | B2 | 4/2004 | Gerber et al. |
| 6,758,849 | B1 | 7/2004 | Michelson |

(Continued)

OTHER PUBLICATIONS

European Search Report dated Feb. 26, 2014 in European Application No. 13 19 2849.

*Primary Examiner* — Jan Christopher Merene
*Assistant Examiner* — Steven Cotroneo
(74) *Attorney, Agent, or Firm* — Carter, DeLuca, Farrell & Schmidt, LLP (57) ABSTRACT An instrument for inserting a spinal implant into an intervertebral space is disclosed. The instrument includes an elongated body having inner and outer shafts configured to longitudinally translate with respect to each other, a holding tip which is configured to articulate with respect to the elongated body in response to the longitudinal translation of the inner and outer shafts, and a driveshaft assembly configured to cooperate with the articulation of the holding tip and secure a spinal implant to the instrument. A spinal implant and a system for inserting a spinal implant into an intervertebral space including an insertion instrument and a spinal implant are also disclosed.

20 Claims, 10 Drawing Sheets

(56) References Cited

U.S. PATENT DOCUMENTS

| | | |
|---|---|---|
| 6,827,740 B1 | 12/2004 | Michelson |
| 6,830,574 B2 | 12/2004 | Heckele et al. |
| 6,852,127 B2 | 2/2005 | Varga et al. |
| 6,923,814 B1 | 8/2005 | Hildebrand et al. |
| 7,156,875 B2 | 1/2007 | Michelson |
| 7,470,273 B2 | 12/2008 | Dougherty-Shah |
| 7,500,991 B2 | 3/2009 | Bartish, Jr. et al. |
| 7,503,933 B2 | 3/2009 | Michelson |
| 7,572,276 B2 | 8/2009 | Lim et al. |
| 7,575,580 B2 | 8/2009 | Lim et al. |
| 7,608,080 B2 | 10/2009 | Shipp et al. |
| 7,611,536 B2 | 11/2009 | Michelson |
| 7,763,078 B2 | 7/2010 | Peterman et al. |
| 7,892,239 B2 | 2/2011 | Warnick et al. |
| 7,901,458 B2 | 3/2011 | DeRidder et al. |
| 7,967,863 B2 | 6/2011 | Frey et al. |
| 7,976,549 B2 | 7/2011 | Dye et al. |
| 7,988,734 B2 | 8/2011 | Peterman et al. |
| 2004/0024406 A1* | 2/2004 | Ralph et al. ............... 606/90 |
| 2007/0093850 A1* | 4/2007 | Harris et al. .............. 606/99 |
| 2008/0306489 A1* | 12/2008 | Altarac et al. ............ 606/99 |
| 2009/0112220 A1 | 4/2009 | Kraus |
| 2009/0216330 A1 | 8/2009 | Geisert et al. |
| 2009/0234364 A1 | 9/2009 | Crook |
| 2010/0256764 A1* | 10/2010 | Tsuang et al. ............ 623/17.16 |
| 2012/0088979 A1* | 4/2012 | Nunley et al. ............ 600/231 |
| 2012/0232660 A1* | 9/2012 | Davenport ............... 623/17.16 |

* cited by examiner

ADJUSTABLE SPINAL IMPLANT INSERTION INSTRUMENT

BACKGROUND

1. Technical Field

The present disclosure relates to apparatus and systems for orthopedic spine surgery and, in particular, to an apparatus for inserting a spinal implant into an intervertebral space.

2. Description of Related Art

The human spine is comprised of thirty-three vertebrae and twenty-four as an adult. An infant contains 7 cervical vertebrae, 12 dorsal or thoracic vertebrae, 5 lumbar vertebrae, 5 sacral vertebrae, and 4 coccygeal or caudal vertebrae. In an adult, the 5 sacral vertebrae fuse together to form the sacrum and the 4 coccygeal vertebrae fuse to form the coccyx. Intervertebral discs lie between each pair of adjacent vertebrae. Every intervertebral disc maintains a space between adjacent vertebrae and acts as cushion under compressive, bending, and rotational loads and motions. Each intervertebral disc has a fibrocartilaginous central portion called the nucleus pulposus. The nucleus pulposus of a healthy intervertebral disc contains significant amount of water. This water content provides spongy quality and allows it to absorb spinal stress.

Each intervertebral disc has an annulus fibrosus, which condition might be affected by the water content of the nucleus pulposus. The annulus fibrosus consist of a ring of fibrocartilage and fibrous tissue forming the circumference of the intervertebral disc. Excessive pressure or injuries to the intervertebral discs may adversely affect the annulus fibrosus. Usually, the annulus fibrosus is the first portion of the intervertebral discs that is injured. The annulus fibrosus may be injured in several ways. Typically, the annulus fibrosus tears due to an injury. When these tears heal, scar tissue forms in the annulus fibrosus. Given that scar tissue is not as strong as normal ligament tissue, the annulus becomes weaker as more scar tissue forms. An annulus fibrosus with scar tissue is usually weaker than a normal annulus fibrosus. The formation of scar tissue may eventually lead to damage to the nucleus pulposus. As a result of this damage, the nucleus fibrosus may, for instance, lose water content, hindering the intervertebral disc's ability to act as a cushion. The reduced cushioning capability might increase stresses on the annulus fibrosus and, consequently, cause still more tears. Hence, the annulus fibrosus may undergo a degenerative cycle consisting of exponential reduction of water content. Eventually, the nucleus pulposus may lose all its water. As the nucleus pulposus loses its water content, it collapses and thus allows the vertebrae above and below the disc space to move closer to each other. In other words, the intervertebral disc space narrows as the nucleus pulposus loses water. When the nucleus pulposus collapses, the facet joints, which are located on the back of the spine, shift, altering the way these joints work together.

When a disc or vertebra is damaged due to disease or injury, performing a spinal fusion is one of the techniques used for treating the patient. During spinal fusion, a surgeon removes part or all of the intervertebral disc, inserts a natural or artificial disc spacer, and constructs an artificial structure to hold the affected vertebrae in place. While the spinal fusion may address the diseased or injured anatomy, the natural biomechanics of the spine are affected in a unique and unpredictable way.

There remains a need for an instrument for inserting spinal implants which provides greater control of the spinal implant during insertion.

SUMMARY

The present disclosure relates to an insertion instrument for placing a spinal implant into an intervertebral space, a spinal implant, and a system for inserting the spinal implant in an intervertebral space using the insertion instrument.

The insertion instrument includes an elongated body having an inner and outer shaft; a tip assembly having an inner shaft tip, an outer shaft tip, and a holding tip; a handle assembly; an articulation assembly; and a driveshaft assembly. The articulation assembly is configured to translate the inner shaft in relation to the outer shaft. The relative translation of the inner shaft and the outer shaft induces translation of the inner shaft tip and the outer shaft tip with respect to each other. The translation of the inner shaft tip and the outer shaft tip induces articulation of the holding tip in relation to the elongated body defining an angle of articulation. The driveshaft assembly extends through a bore within the elongated body, the tip assembly, and the holding tip. The driveshaft assembly is configured to secure a spinal implant to the distal end of the holding tip.

In an embodiment of the insertion instrument, the driveshaft assembly includes a coupling knob, a coupling shaft, a torque limiter, and a universal joint. The universal joint cooperates with the articulation of the holding tip with respect to the elongated body. The distal end of the universal joint is threaded to secure the implant to the insertion instrument.

In another embodiment of the insertion instrument, the handle assembly is rotatable about elongated body. The handle assembly is configured to lock in a selected radial position with respect to the elongated body.

In one embodiment of the spinal implant, the spinal implant is generally convex between the leading and trailing ends. The leading end of the implant is generally bullet shaped and has a blunt tip. The sidewalls of the implant may share a radii of curvature. The top and the bottom of the implant may have two sets of teeth. The first set of teeth is located near the leading end of the implant. The first set of teeth has ridges substantially parallel to the sidewalls sharing the radii of curvature. The second set of teeth is located near the trailing end of the body. The second set of teeth has ridges substantially perpendicular to the sidewalls with a vertical face open to the trailing end. The trailing end of the spinal implant has a threaded opening. At least one sidewall has a groove.

In an embodiment for the system for inserting a spinal implant into an intervertebral space with an insertion instrument, the system includes the insertion instrument and the spinal implant discussed above. The trailing end of the spinal implant configured to cooperate with the distal end of the holding tip and the distal end of the driveshaft assembly. The spinal implant is secured to the holding tip by the rotation of the driveshaft assembly. The torque limiter in the driveshaft assembly is configured to limit the rotation of the driveshaft assembly when the spinal implant is secured to the holding tip.

BRIEF DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION OF THE EMBODIMENTS

Particular embodiments of the present disclosure will be described herein with reference to the accompanying drawings. As shown in the drawings and as described throughout the following description, and as is traditional when referring to relative positioning on an object, the term "proximal" or "trailing" refers to the end of the apparatus that is closer to the user and the term "distal" or "leading" refers to the end of the apparatus that is farther from the user. In the following description, well-known functions or constructions are not described in detail to avoid obscuring the present disclosure in unnecessary detail.

Figure 1:
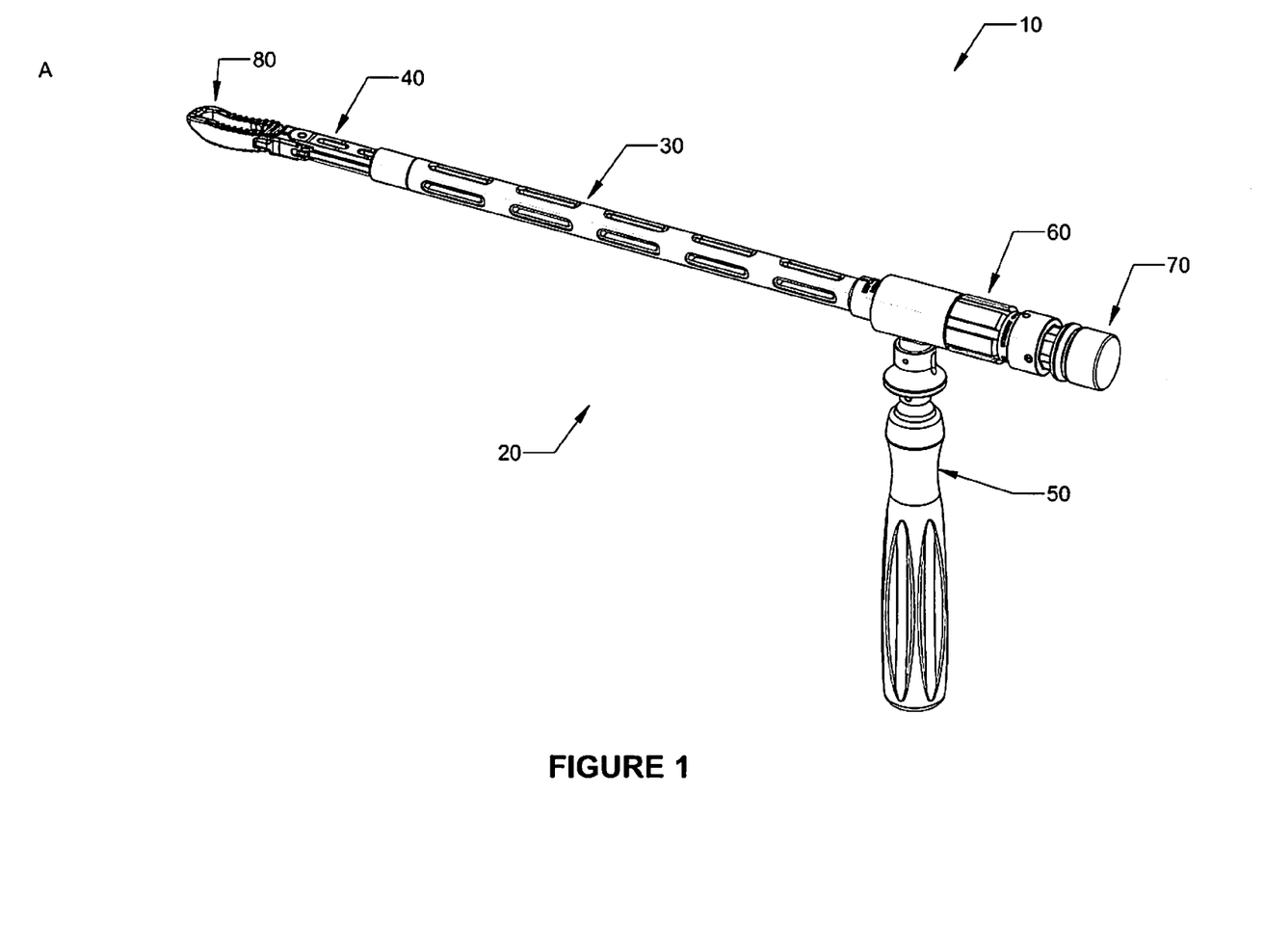
FIG. 1 is a perspective view showing the system for inserting a spinal implant into an intervertebral space with an insertion instrument with the spinal implant secured to the insertion instrument.
Figure 2:
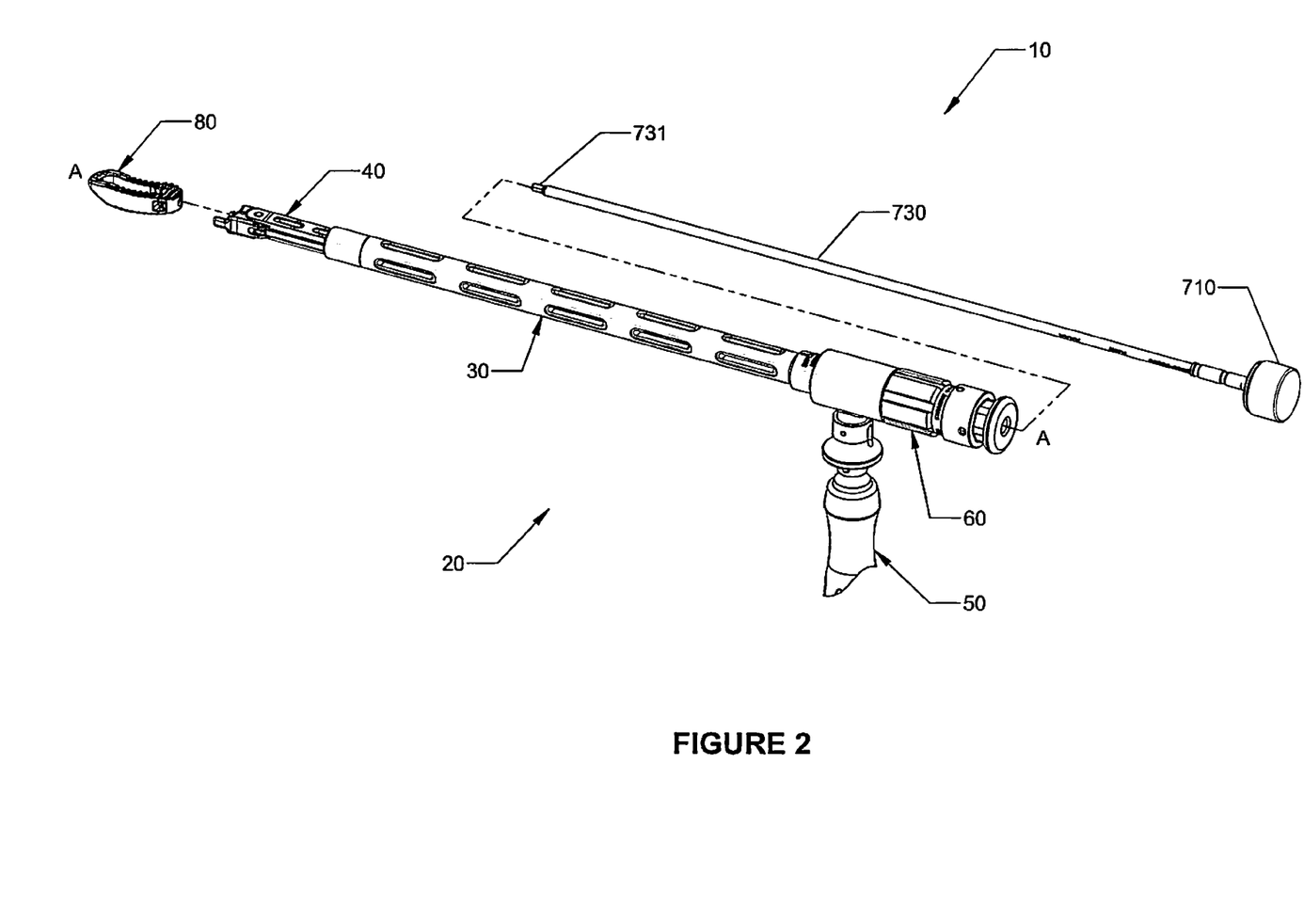
FIG. 2 is a perspective view showing the system for inserting a spinal implant into an intervertebral space with an insertion instrument with the coupling shaft removed and the spinal implant free.

Referring now to the drawings, in which like reference numerals identify identical or substantially similar parts throughout the several views, FIGS. 1 and 2 illustrate an embodiment of system 10 for inserting a spinal implant into an intervertebral space with an insertion instrument.

Figure 3:
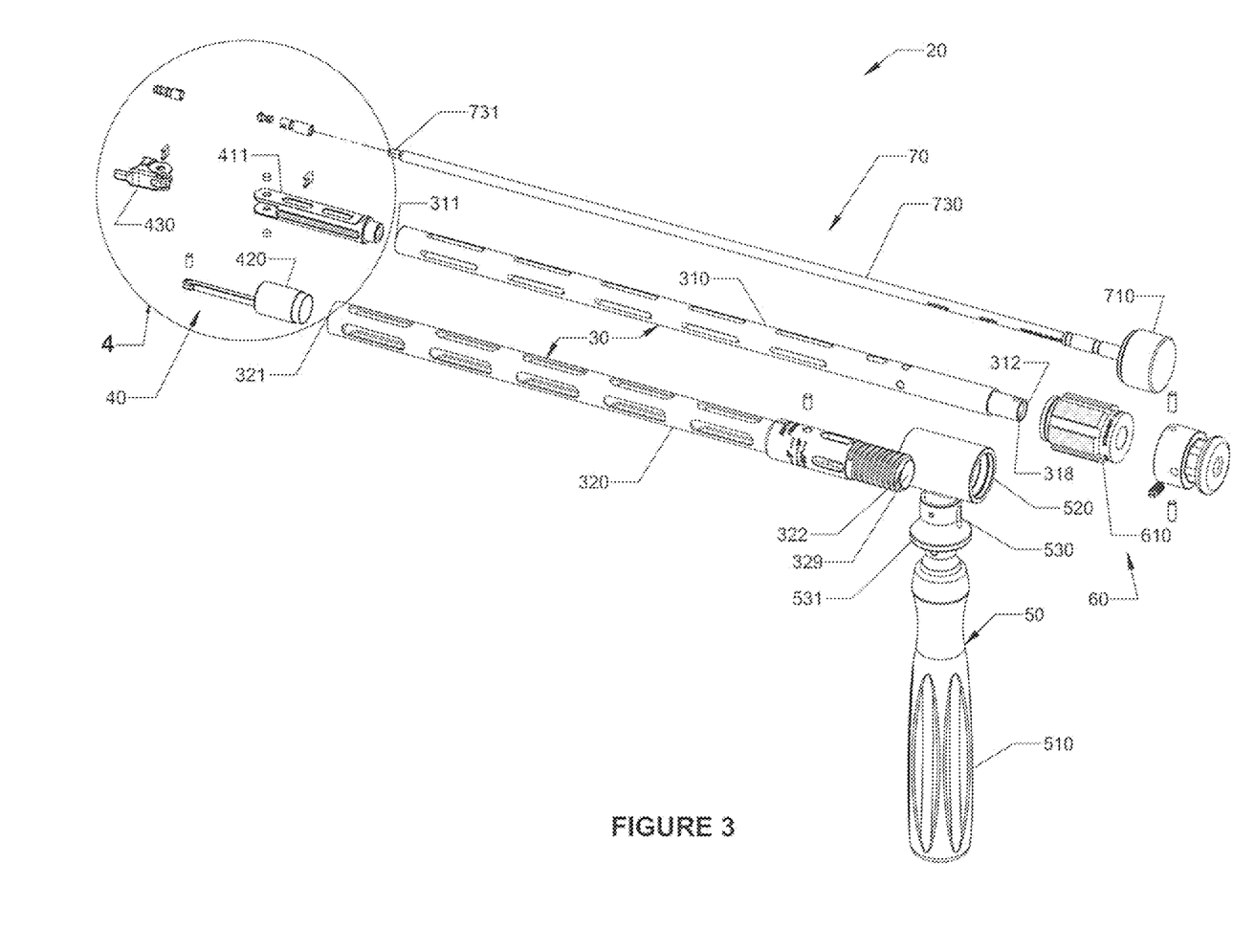
FIG. 3 is an exploded view, with parts separated, of the insertion instrument of FIG. 1.
Figure 5:
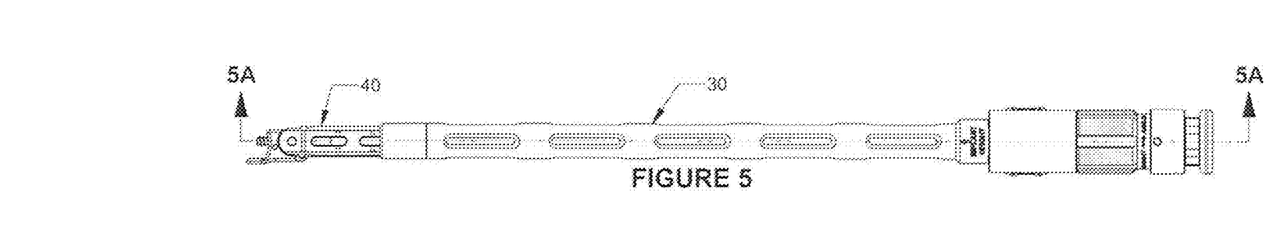
FIG. 5 is a top view of the insertion instrument in the straight configuration.
Figure 5A:
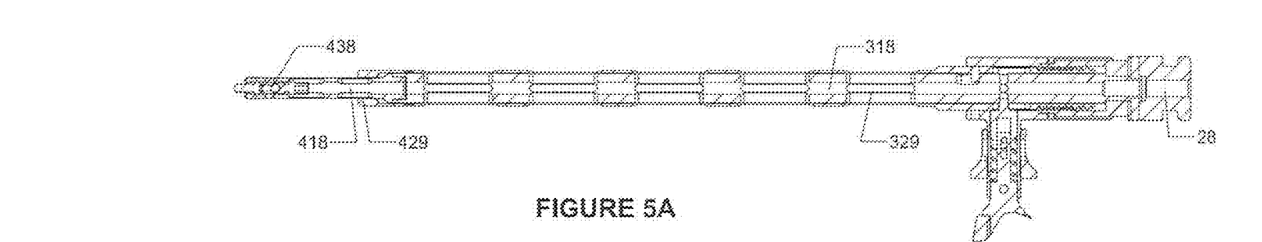
FIG. 5A is a side cross-section view of the insertion instrument of FIG. 5 taken along section line 5A-5A.

The embodiment of insertion instrument 20 shown in FIG. 3 includes elongated body 30, tip assembly 40, handle assembly 50, articulation assembly 60, and driveshaft assembly 70. Elongated body 30 defines longitudinal axis A-A (FIG. 1). Elongated body 30 includes inner shaft 310 and outer shaft 320. Inner shaft 310 has open distal and proximal ends 311, 312 which define first passage 318 therethrough. Outer shaft 320 has open distal and proximal ends 321, 322 which define first lumen 329 therethrough (FIG. 5A). Inner shaft 310 is at least partially disposed within first lumen 329.

Figure 4:
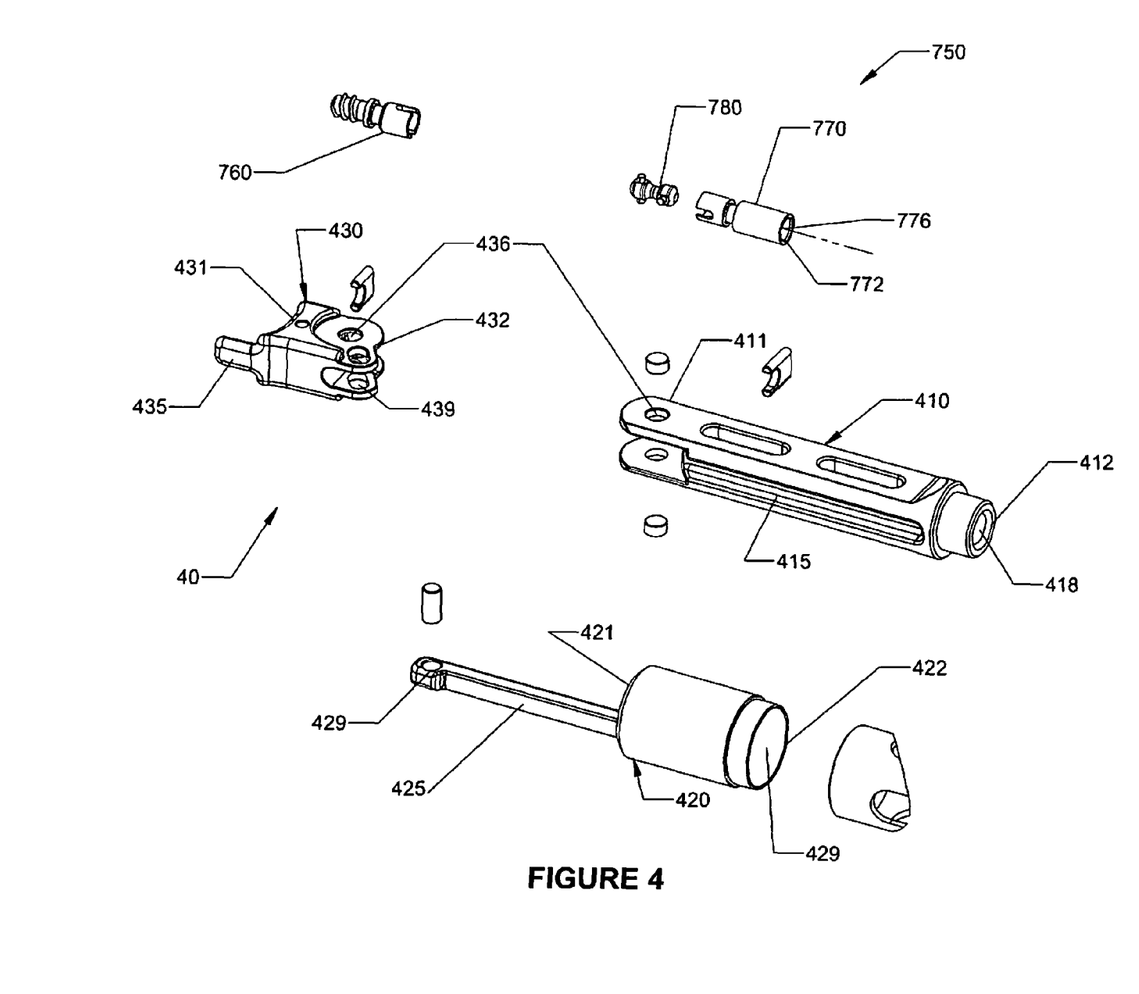
FIG. 4 is an enlarged view of the detail area 4 of FIG. 3.

Now referring to FIG. 4, tip assembly 40 includes inner shaft tip 410, outer shaft tip 420, and holding tip 430. Outer shaft tip 420 has open distal and proximal ends 421, 422 which define second lumen 429 therethrough. Outer shaft tip 420 includes distally extending arm 425. Inner shaft tip has second passage 418 therethrough and recessed area 415. Inner shaft tip 410 is at least partially disposed within second lumen 429. Distally extending arm 425 is slidably received in recessed area 415. Proximal end of the inner shaft tip 412 is positioned at distal end of the inner shaft 311. Proximal end of the outer shaft tip 422 is positioned at distal end of the outer shaft 321.

Holding tip 430 has third passage 438 therethrough (FIG. 5A). Referring back to FIG. 4, proximal end of the holding tip 432 is coupled to distal end of the inner shaft tip 411 by articulating connection 436. Distal end of the distally extending arm 429 is coupled to the proximal end of the holding tip to offset hole 439 at the distal end of the holding tip 431. Holding tip 430 may include distally extending finger 435 offset from the center of holding tip 430.

Figure 9:
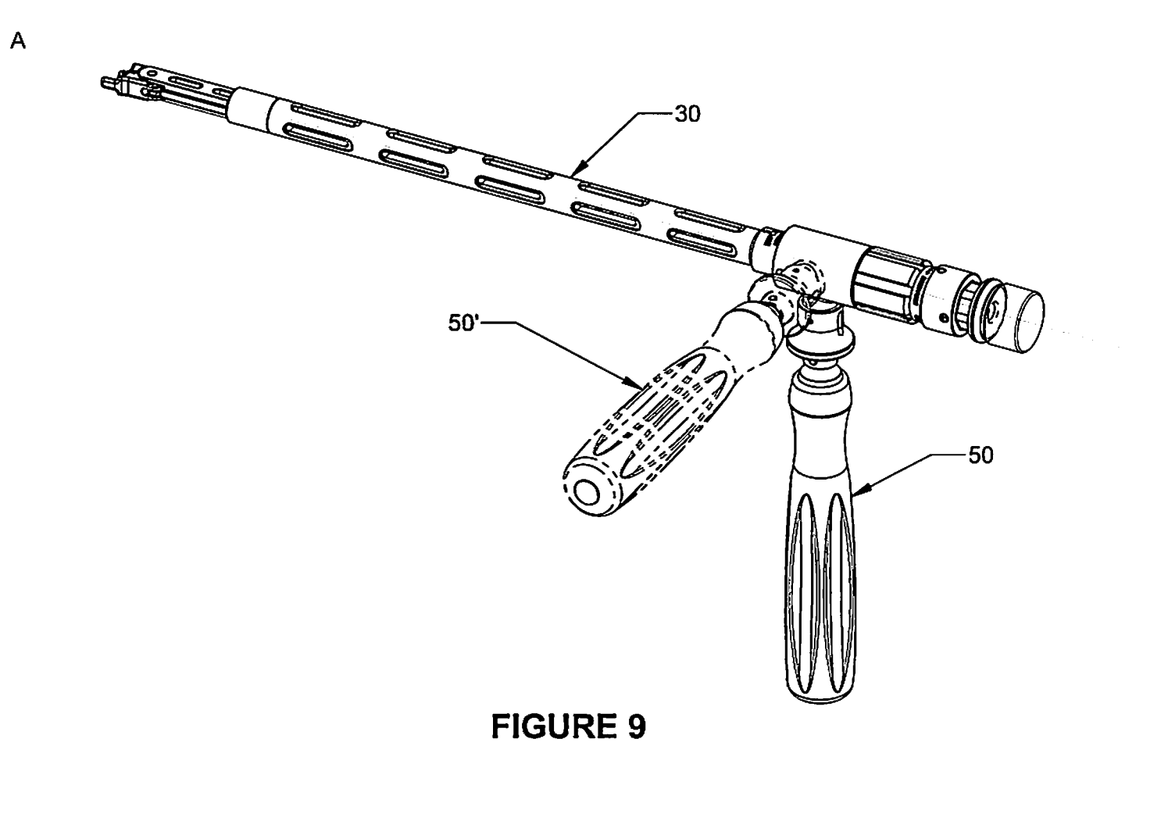
FIG. 9 is a perspective view of the insertion instrument showing the handle assembly configured to rotate about the elongated body.

Referring now to FIGS. 3 and 9, handle assembly 50 includes handle 510 and body portion 520. Body portion 520 is coaxially aligned with elongated body 30. Body portion 520 is coupled to the proximal end of the outer shaft 322. Handle 510 is substantially orthogonal to longitudinal axis A-A. Handle 510 may be rotatable a full 360° about longitudinal axis A-A.

In a particular embodiment, handle assembly 50 includes locking mechanism 530 to lock handle assembly 50 in a radial position in relation to longitudinal axis A-A. Locking mechanism 530 may be collar 531 located on handle 510. Locking mechanism 530 may be selectively engagable. Handle 510 may have predefined radial positions and a means for engaging the locking mechanism 530 at each of the predefined radial positions.

Figure 6:
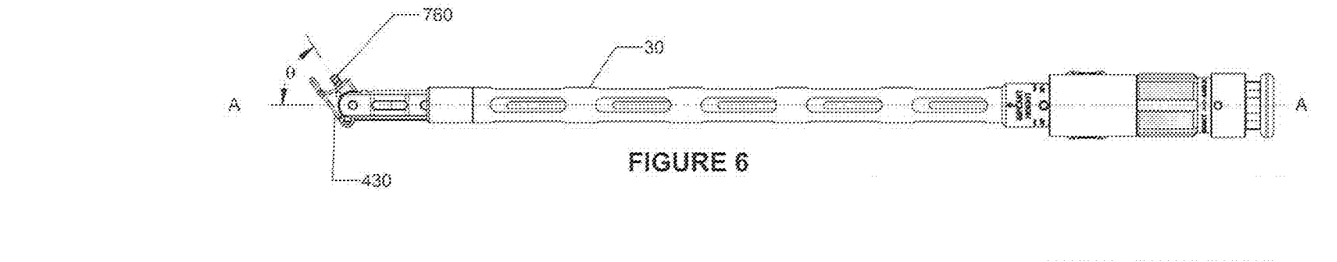
FIG. 6 is a top view of the insertion instrument in an articulated configuration.
Figure 7:
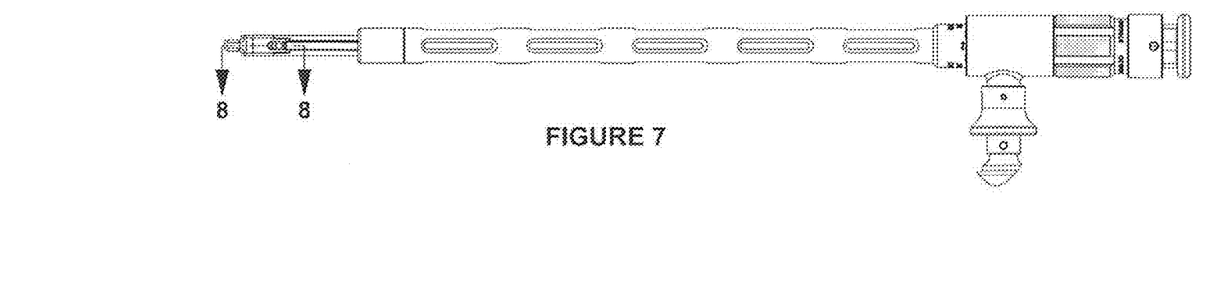
FIG. 7 is a side view of the insertion instrument in the straight configuration.
Figure 8:
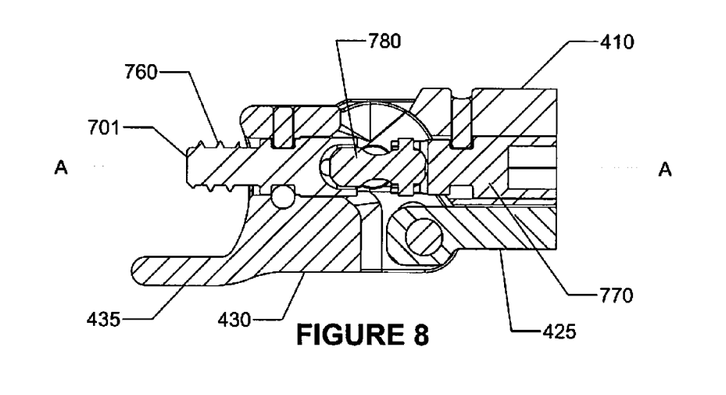
FIG. 8 is a bottom cross-section view taken along section line 8-8 of the distal portion of the instrument of FIG. 7.
Figure 8A:
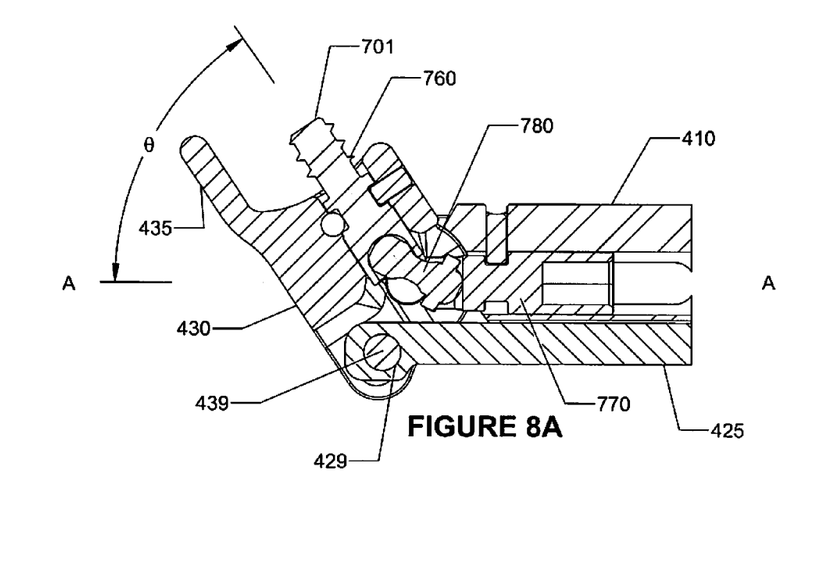
FIG. 8A is an articulated configuration of the distal portion shown in FIG. 8.

Referring back to FIGS. 2 and 3, articulation assembly 60 includes articulation knob 610. Articulation knob 610 is coupled to inner shaft 310. Rotational movement of articulation knob 610 about longitudinal axis A-A induces longitudinal translation of outer shaft 320 in relation to inner shaft 310. Outer shaft tip 420 and inner shaft tip 410 cooperate with the translation of outer shaft 320 and inner shaft 310, respectively, as shown in FIGS. 8 and 8A. The translation of outer shaft tip 320 with respect to inner shaft tip 310 results in the articulation of holding tip 430 with respect to elongated body 30. The articulation of holding tip 430 defines angle of articulation θ as shown in FIGS. 6 and 8A.

In an embodiment of insertion instrument 20, angle of articulation θ has a minimum angle of articulation and a maximum angle of articulation. The minimum angle of articulation is about 0°, defining a substantially straight configuration as shown in FIG. 5. The maximum angle of articulation is about 60°. Any angle of articulation other than 0° defines an articulated configuration as is illustrated in FIG. 6.

In another embodiment of insertion instrument 20, when articulation knob 610 is rotated in a first direction, holding tip 430 transitions from a minimum angle of articulation to a maximum angle of articulation. Once the maximum angle of articulation is reached, articulation knob 610 cannot rotate any further in the first direction.

In an embodiment of articulation assembly 60, articulation knob 610 has marked angles of articulation 620. The outer surface of articulation knob 610 has indicia for each of the marked angles of articulation 620 of the holding tip.

Now referring to FIG. 5A, first, second, and third passages 318, 418, 438 are capable of axial alignment. When three passages 318, 418, 438 are in axial alignment, bore 28 through insertion instrument 20 is defined.

Referring to FIG. 3, driveshaft assembly 70 includes coupling knob 710 on proximal end of the driveshaft assembly and a shaft extending distally from coupling knob 710. The distally extending shaft is configured to extend through bore 28. Distal end of the driveshaft assembly 701 extends or protrudes from distal end of the holding tip 431 as shown in FIGS. 8 and 8A. Driveshaft assembly 70 may be flexible to cooperate with the articulation of holding tip 430 with respect to elongated body 30. Driveshaft assembly 70 cooperates with the rotation of coupling knob 710.

In an embodiment shown in FIGS. 3 and 4, driveshaft assembly 70 further includes universal joint 750 and coupling shaft 730. Universal joint 750 includes threaded distal end 760, articulating member 780, and proximal end 770. Threaded distal end 760 is at least partially disposed within third passage 438 with the threaded distal tip 701 extending or protruding from distal end of the holding tip 430 as shown in FIG. 8. Articulating member 780 is disposed within at least second and third passages 418, 438 cooperating with angle of articulation θ as shown in FIG. 8A. Proximal end of the universal joint 770 is at least partially disposed within second passage 418 and is configured to couple with coupling shaft 730. Coupling shaft 730 extends distally from coupling knob 710. Coupling shaft 730 configured to traverse at least first passage 318 and couple to the proximal end of the proximal end of the universal joint 772.

In another embodiment shown in FIGS. 3 and 4, coupling shaft 730 includes hexagonal distal end 731. Proximal end of the universal joint 770 includes hexagonal opening 776. The hexagonal distal end of the coupling shaft 731 is configured to cooperate with the hexagonal opening 776. Further, coupling shaft 730 is made of a rigid material. The cooperation of coupling shaft 730 and universal joint 750 allows coupling shaft 730 to be selectively removable from first passage 318. Coupling shaft 730 cooperates with the rotation of coupling knob 710. In this embodiment, when coupling shaft 730 traverses first passage 318 hexagonal distal end of the coupling shaft 731 contacts the proximal end universal joint 770, rotation of coupling knob 710 causes coupling shaft 730 to couple to universal joint 750. Continued rotation of coupling knob 710 induces rotation of universal joint 750, causing threaded distal end of the universal joint 760 to rotate. Coupling knob 710 may include a torque limiter such that at a preset torque continued rotation of coupling knob 710 no longer induces rotation of coupling shaft 730. Universal joint 750 is configured to rotate at any angle of articulation θ.

FIGS. 13-17 show an embodiment of spinal implant 80. Spinal implant 80 includes body 800 with substantially contoured first end surface 810 at leading end 801 and second end surface 820 opposite thereto at trailing end 802. Body 800 extends between first and second end surfaces 810, 820 to define top and bottom engaging surfaces 803, 804. Top and bottom engaging surfaces 803, 804 are opposite one another. Body further defines sidewalls 805. Sidewalls 805 are substantially parallel to one another and have a common radius of curvature.

Figure 16:
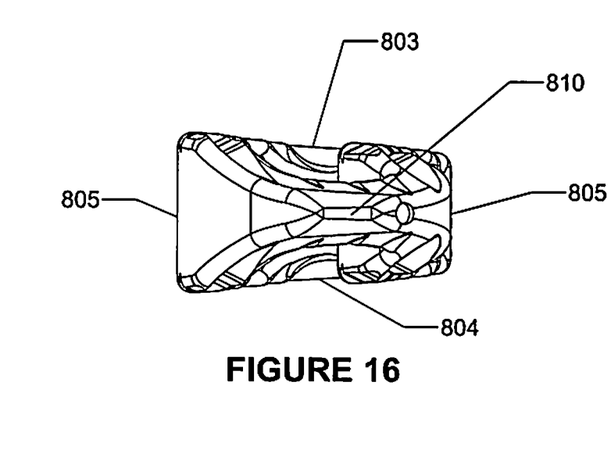
FIG. 16 is a front view of the spinal implant from the leading end.
Figure 17:
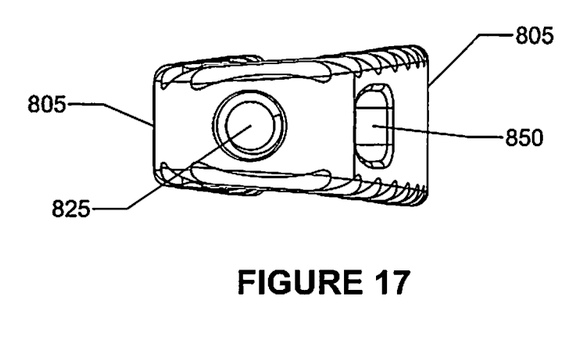
FIG. 17 is a back view of the spinal implant from the trailing end.

Body 800 is configured such that top and bottom engaging surfaces 803, 804 intersect with sidewalls 805 forming a substantially trapezoidal cross-section with rounded corners as shown in FIGS. 16 and 17. Top and bottom engaging surfaces 803, 804 converge towards the radii of curvature.

Body 800 is configured such that top and bottom engaging surfaces 803, 804 have a substantially streamlined convex profile. Further, body 800 is configured such that at least one of the top and bottom engaging surfaces 803, 804 has at least first and second surface regions 806, 807 having distinct surface characteristics as shown in FIG. 15.

Figure 15:
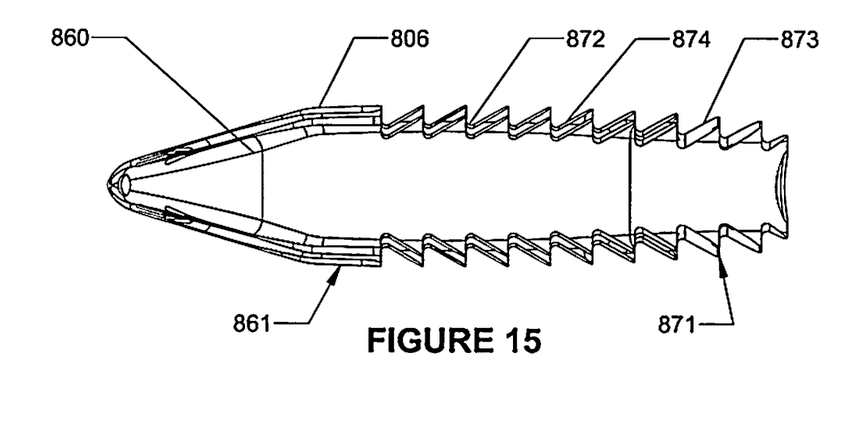
FIG. 15 is a side view of the spinal implant.

Still referring to FIG. 15, top and bottom engaging surfaces 803, 804 and sidewalls 805 converge at leading end 801 to define blunt nose 810, shown in FIG. 16. Blunt nose 810 has a tip with substantially planar surfaces 860 on top and bottom engaging surfaces 803, 804 and a rounded shape defined by sidewalls 805. Substantially planar surfaces 860 define first surface region 806 while second surface region 807 is proximal to first surface region 806 on each of top and bottom engaging surfaces 803, 804.

In an embodiment, the surface characteristic of first surface region 806 includes a plurality of protrusions having a first configuration. The surface characteristic of second surface region 807 includes a plurality of protrusions having a second configuration distinct from that of first surface region 806.

Figure 14:
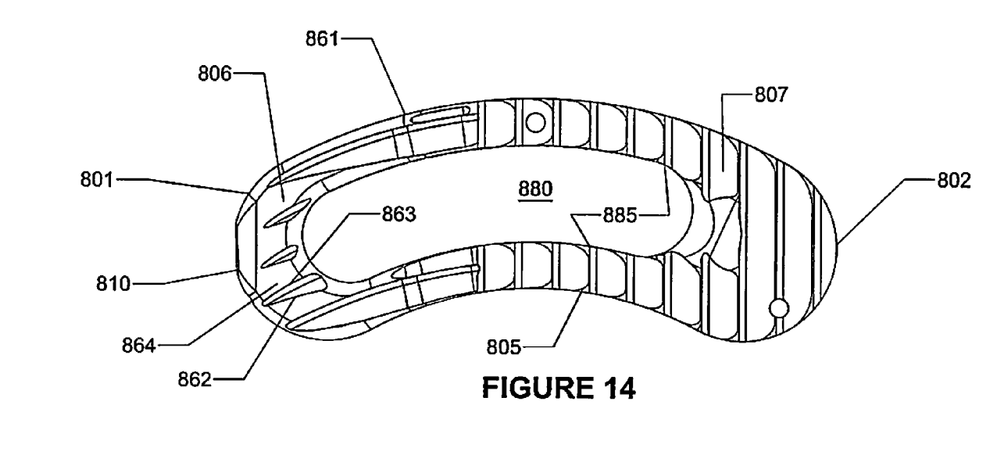
FIG. 14 is a top view of the spinal implant.

Referring now to FIG. 14, the configuration of the plurality of protrusions of first surface region 806 may define first set of ridges 861. Each ridge of first set of ridges 861 has a position along at least one of top and bottom engaging surfaces 803, 804. Each ridge of first set of ridges 861 includes first ridge face 862 substantially orthogonal to at least one of top and bottom engaging surfaces 803, 804 and substantially parallel to sidewalls 805. Each ridge of first set of ridges 861 includes second opposing ridge face 863 defining channel 864 between first ridge face 862 and second opposing ridge face 863. Channel 864 may be flat or grooved.

Referring now to FIG. 15, the plurality of protrusions of second surface region 807 defines a set of saw tooth protrusions 871. Each of saw tooth protrusions 871 has a position along at least one of top and bottom engaging surfaces 803, 804. Each of saw tooth protrusions 871 has first tooth face 872 substantially orthogonal to top and bottom engaging surfaces 803, 804 and substantially parallel to trailing surface 820. Each of saw tooth protrusions 871 defines second opposing tooth face 873. First tooth face 872 and second tooth face 873 define bone engagement region 874 between the tooth faces 872, 873.

Now referring back to FIG. 14, in a particular embodiment, spinal implant 80 includes body 800 with at least one opening 880 extending through body 800. Opening 880 may extend through top and bottom engaging surfaces 803, 804. Further, inner sidewalls 885 of opening 880 may share the radii of curvature with sidewalls 805.

In a preferred embodiment shown in FIG. 17, spinal implant 80 has threaded opening 825 in trailing surface 820. Further, spinal implant 80 grooved depression 850 on at least one of sidewalls 805 near trailing end 802.

Figure 10:
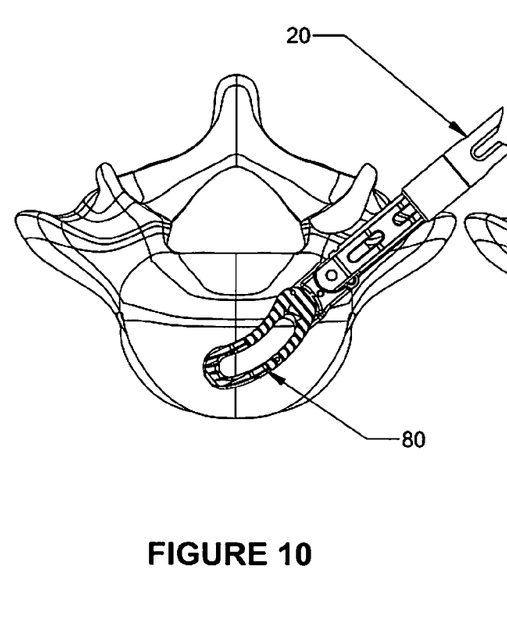
FIG. 10 shows the system being used to insert the spinal implant, which is secured to the insertion instrument by the driveshaft assembly, into an intervertebral space, the insertion instrument in the straight configuration.
Figure 11:
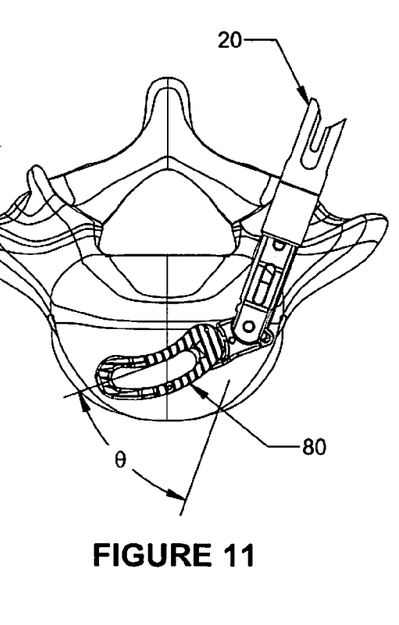
FIG. 11 shows the system being used to insert the spinal implant, which is secured to the insertion instrument by the driveshaft assembly, into an intervertebral space, the insertion instrument in an articulated configuration.
Figure 12:
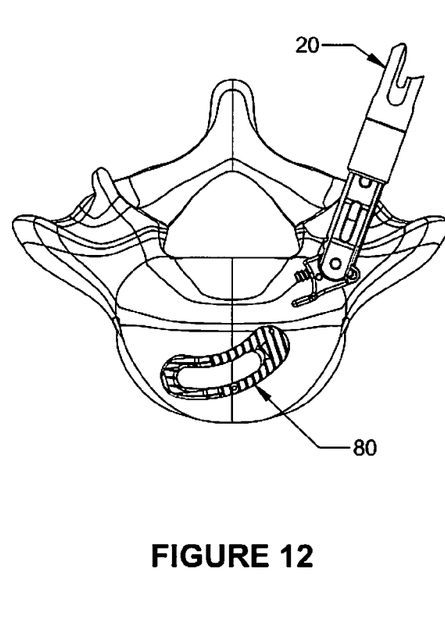
FIG. 12 shows the system being used to insert the spinal implant into an intervertebral space, the spinal implant free from insertion instrument and the insertion instrument in an articulated configuration.
Figure 13:
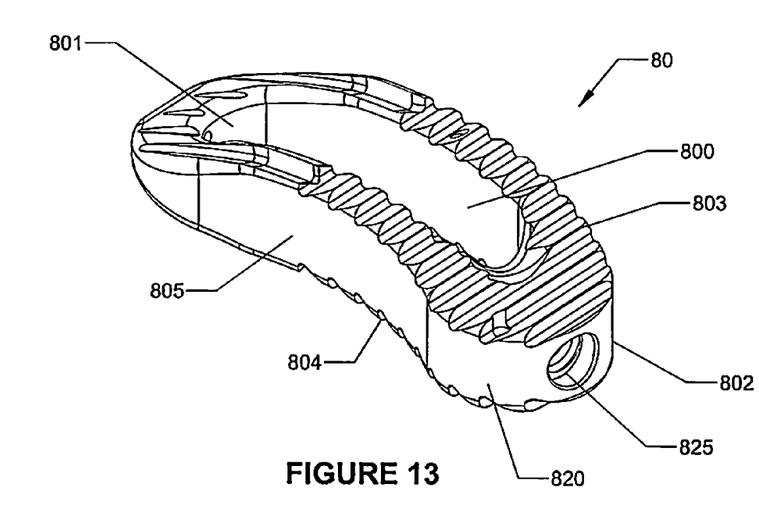
FIG. 13 is a perspective view of the spinal implant.

In an embodiment of system 10 for inserting a spinal implant in an intervertebral space with an insertion instrument, system 10 includes spinal implant 80 and insertion instrument 20 configured to cooperate as discussed in detail below and shown in FIGS. 10-12.

System 10 includes spinal implant 80 having threaded opening 825 configured to receive distal end of the driveshaft assembly 701. Threaded opening 825 and distal end of the driveshaft assembly 701 each threaded in a manner such that the threads cooperate to threadably couple driveshaft assembly 70 to spinal implant 80. When spinal implant 80 is secured to distal end of the holding tip 431 by driveshaft assembly 70 a coupling torque is defined. The coupling torque may be used to limit continued rotation of driveshaft assembly 70 when spinal implant 80 is secured to distal end of the holding tip 431.

In an embodiment, insertion instrument 20 includes distally extending finger 435 configured to engage grooved depression 850 in at least one sidewalls 805. Thus securing spinal implant 80 in position with respect to holding tip 430.

System 10 may include insertion instrument 20 where holding tip 430 is configured to articulate with respect to elongated body 30 defining an angle of articulation θ. Further, insertion instrument 20 may be configured to selectively receive or release spinal implant 80 without regard to angle of articulation θ.

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Different embodiments of the disclosure may be combined with one another based on the particular needs of the patients to achieve optimal results of the surgical procedures. Those skilled in the art will envision other modifications within the scope and spirit of the claims appended hereto.

What is claimed is:

1. A surgical instrument to implant prosthetic spinal implants, comprising:

an elongated body having an inner shaft and an outer shaft defining a longitudinal axis, the outer shaft having open distal and proximal ends forming a first lumen therethrough, the inner shaft disposed within the first lumen of the outer shaft, the inner shaft having open distal and proximal ends defining a first passage therethrough;

a handle assembly having a handle and a body portion, the body portion being coaxially aligned with the elongated body, the body portion coupled to the proximal end of the outer shaft, the handle orthogonal to the longitudinal axis;

a tip assembly with an outer shaft tip, an inner shaft tip, and a holding tip, the outer shaft tip having open proximal and distal ends defining a second lumen therethrough, the outer shaft tip having a distally extending arm, the inner shaft tip having a second passage therethrough, the inner shaft tip having a recessed area, the holding tip having a third passage therethrough, the inner shaft tip disposed within the second lumen of the outer shaft tip, the distally extending arm slidably received in the recessed area of the inner shaft tip, the recessed area being defined along a majority of the length of the inner shaft tip parallel to the longitudinal axis, a proximal end of the inner shaft tip positioned at the distal end of the inner shaft, a proximal end of the holding tip coupled to a distal end of the inner shaft tip by an articulating connection, a distal end of the distally extending arm coupled to the holding tip, the first, second, and third passages capable of axial alignment;

an articulation knob coupled to the inner shaft, where rotational movement of the articulation knob about the longitudinal axis induces longitudinal translation of the outer shaft in relation to the inner shaft causing translation of the outer shaft tip in relation to the inner shaft tip resulting in articulation of the holding tip with respect to the elongated body thereby defining an angle of articulation; and a driveshaft assembly having proximal and distal ends, the proximal end having a coupling knob, the distal end having a threaded tip, the driveshaft assembly extending distally through the first passage, the second passage, and the third passage, the threaded tip extending distally from the holding tip.

2. The instrument of claim 1, wherein the driveshaft assembly is further comprised of a universal joint and a coupling shaft, the universal joint including the threaded tip of the drive shaft, an articulating member, and a proximal end, the universal joint disposed within at least the second and third passages cooperating with the articulation of the inner shaft tip and the holding tip, the coupling shaft disposed within at least the first passage, the coupling shaft extending distally from the coupling knob, the distal end of the coupling shaft coupled to the proximal end of the universal joint.

3. The instrument of claim 2, wherein the coupling shaft is made of a rigid material.

4. The instrument of claim 3, wherein the coupling shaft has a hexagonal end and the proximal end of the universal joint has a hexagonal opening configured to receive the hexagonal end.

5. The instrument of claim 4, wherein the coupling shaft is removable from the first passage without disassembly of the instrument.

6. The instrument of claim 1, wherein the driveshaft assembly is removable from the first passage without disassembly of the instrument.

7. The instrument of claim 1, further comprising a torque limiter.

8. The instrument of claim 1, wherein the handle assembly is rotatable about the longitudinal axis.

9. The instrument of claim 8, wherein the handle assembly further comprises a locking mechanism to lock the handle assembly in a radial position in relation to the longitudinal axis.

10. The instrument of claim 9, wherein the locking mechanism is a collar located on the handle.

11. The instrument of claim 1, wherein the holding tip further comprises a distally extending finger offset from a center of the holding tip.

12. The instrument of claim 1, wherein the angle of articulation is between 0 degrees and 60 degrees.

13. The instrument of claim 1, wherein the holding tip and the inner shaft tip are coupled by two cooperating pivot pins.

14. The instrument of claim 1, wherein the articulation knob has indicia of angles of articulation.

15. The instrument of claim 1, wherein the rotation of the articulation knob transitions the holding tip from a minimum angle of articulation towards a maximum angle of articulation such that once the maximum angle of articulation is reached, the articulation knob no longer rotates.

16. The instrument of claim 1, wherein rotational movement of the articulation knob about the longitudinal axis induces longitudinal translation of the outer shaft in relation to the longitudinal axis causing the longitudinal translation of the outer shaft tip in relation to the longitudinal axis.

17. A system for inserting a spinal implant in an intervertebral space, comprising:

a surgical instrument including:

an elongated body having an inner shaft and an outer shaft defining a longitudinal axis, the outer shaft having open distal and proximal ends forming a first lumen therethrough, the inner shaft disposed within the first lumen of the outer shaft, the inner shaft having open distal and proximal ends defining a first passage therethrough;

a handle assembly having a handle and a body portion, the body portion being coaxially aligned with the elongated body, the body portion coupled to the proximal end of the outer shaft, the handle orthogonal to the longitudinal axis;

a tip assembly with an outer shaft tip, an inner shaft tip, and a holding tip, the outer shaft tip having open proximal and distal ends defining a second lumen therethrough, the outer shaft tip having a distally extending arm, the inner shaft tip having a second passage therethrough, the inner shaft tip having a recessed area, the holding tip having a third passage therethrough, the inner shaft tip disposed within the second lumen of the outer shaft tip, the distally extending arm slidably received in the recessed area of the inner shaft tip, a proximal end of the inner shaft tip positioned at the distal end of the inner shaft, a proximal end of the holding tip coupled to a distal end of the inner shaft tip by an articulating connection, a distal end of the distally extending arm coupled to the holding tip, the first, second, and third passages capable of axial alignment;

an articulation knob coupled to the inner shaft, where rotational movement of the articulation knob about the longitudinal axis induces longitudinal translation of the outer shaft in relation to the inner shaft causing translation of the outer shaft tip in relation to the inner shaft tip resulting in articulation of the holding tip with respect to the elongated body about the articulating connection of the holding tip and the distal end of the inner shaft thereby defining an angle of articulation; and a driveshaft assembly having proximal and distal ends, the proximal end having a coupling knob, the distal end having a threaded tip, the driveshaft assembly extending distally through the first passage, the second passage, and the third passage, the threaded tip extending distally from the holding tip; and a spinal implant attachable to the surgical instrument.

18. The system of claim 17, wherein the spinal implant has a proximal end and a distal end, the proximal end of the spinal implant threadably coupled to the distal end of driveshaft assembly of the surgical instrument.

19. The system of claim 17, wherein the spinal implant includes sidewalls, at least one sidewall having a grooved depression, the holding tip of the surgical instrument having a distally extending finger offset from a center of the holding tip, the distal extending finger engaging the grooved depression.

20. A surgical instrument to implant prosthetic spinal implants, comprising:

an elongated body having an inner shaft and an outer shaft defining a longitudinal axis, the outer shaft having open distal and proximal ends forming a lumen therethrough, the inner shaft disposed within the lumen of the outer shaft, the inner shaft having open distal and proximal ends defining a first passage therethrough, the inner shaft defining a recessed area which slidably receives a distally extending arm of the outer shaft;

a handle assembly having a handle and a body portion, the body portion being coaxially aligned with the elongated body, the body portion coupled to the proximal end of the outer shaft, the handle orthogonal to the longitudinal axis;

a holding tip defining a second passage therethrough, a proximal end of the holding tip coupled to a distal end of the inner shaft by an articulating connection, the distally extending arm coupled to the holding tip, the first and second passages capable of axial alignment; and an articulation knob coupled to the inner shaft such that rotational movement of the articulation knob about the longitudinal axis induces longitudinal translation of the outer shaft in relation to the inner shaft resulting in articulation of the holding tip with respect to the elongated body about the articulating connection of the holding tip and the distal end of the inner shaft thereby defining an angle of articulation.

* * * * *